United States Patent
Nakano

(10) Patent No.: US 8,693,749 B2
(45) Date of Patent: Apr. 8, 2014

(54) IMAGE PROCESSING APPARATUS AND METHOD

(75) Inventor: Yuta Nakano, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 42 days.

(21) Appl. No.: 13/277,677

(22) Filed: Oct. 20, 2011

(65) Prior Publication Data

US 2012/0134563 A1    May 31, 2012

(30) Foreign Application Priority Data

Nov. 26, 2010 (JP) .................................. 2010-264294

(51) Int. Cl.
*G06K 9/00* (2006.01)
*A61B 3/14* (2006.01)

(52) U.S. Cl.
USPC ........................... 382/128; 382/275; 351/206

(58) Field of Classification Search
USPC ......... 382/100, 103, 106, 117, 128–134, 155, 382/162, 173, 181, 199, 220, 232, 254, 274, 382/275, 276, 305, 312; 351/206; 345/440; 600/425
See application file for complete search history.

(56) References Cited

U.S. PATENT DOCUMENTS

| | | | |
|---|---|---|---|
| 7,905,596 B2 * | 3/2011 | Aoki et al. ..................... | 351/206 |
| 8,408,704 B2 * | 4/2013 | Tomidokoro et al. ......... | 351/206 |
| 8,416,991 B2 | 4/2013 | Everett et al. | |
| 2007/0070295 A1 | 3/2007 | Tsukada et al. | |
| 2007/0285619 A1 | 12/2007 | Aoki et al. | |
| 2010/0194757 A1 * | 8/2010 | Tomidokoro et al. ......... | 345/440 |
| 2010/0290004 A1 | 11/2010 | Huang et al. | |
| 2011/0137157 A1 * | 6/2011 | Imamura et al. .............. | 600/425 |
| 2011/0242484 A1 | 10/2011 | Furukawa et al. | |
| 2012/0063660 A1 * | 3/2012 | Imamura et al. .............. | 382/131 |
| 2012/0308108 A1 | 12/2012 | Everett et al. | |
| 2013/0281841 A1 | 10/2013 | Everett et al. | |

FOREIGN PATENT DOCUMENTS

| | | |
|---|---|---|
| CN | 1939208 A | 4/2007 |
| CN | 101084824 A | 12/2007 |
| EP | 2 189 110 A1 | 5/2010 |
| JP | 2007-325831 A | 12/2007 |
| JP | 2009-507537 A | 2/2009 |
| JP | 2009-066015 A | 4/2009 |
| RU | 2008 137 091 A | 3/2010 |
| RU | 2393755 C2 | 7/2010 |
| WO | 2007/028531 A1 | 3/2007 |
| WO | 2009/061425 A1 | 5/2009 |
| WO | 2010/098204 A1 | 9/2010 |

OTHER PUBLICATIONS

Dec. 26, 2013 Chinese Official Action in Chinese Patent Appln. No. 201110396283.2.

* cited by examiner

*Primary Examiner* — Seyed Azarian

(74) *Attorney, Agent, or Firm* — Fitzpatrick, Cella, Harper & Scinto

(57) ABSTRACT

An image processing apparatus processes a plurality of tomograms obtained by acquiring, along a direction crossing at a right angle a section along the thickness direction of a retina, a plurality of tomograms each including the section. The apparatus detects a layer structure in the retina from image information of respective lines of the tomograms along the thickness direction, and appends structure information to the respective lines based on the layer structures detected for the respective lines. The image processing apparatus maps the structure information of the respective lines of the plurality of tomograms onto a plane crossing the thickness direction at a right angle, thereby generating a two-dimensional image based on the structure information.

26 Claims, 14 Drawing Sheets

IMAGE PROCESSING APPARATUS AND METHOD

BACKGROUND OF THE INVENTION

1. Field of the Invention

The present invention relates to an image processing apparatus and method for supporting imaging of an eye and, more particularly, to an image processing apparatus and method suitable for processing the tomogram of an eye.

2. Description of the Related Art

Ophthalmic examinations are prevalently made aiming at early diagnosis of lifestyle diseases or high-ranking diseases that lead to blindness. An ophthalmic tomography imaging apparatus such as an OCT (Optical Coherence Tomography) apparatus is useful for diagnosis of a disease because it allows three-dimensionally observing the internal state of the retina layer.

FIG. 14 is a schematic view showing tomograms of the macular portion of retina captured by the OCT apparatus. The OCT apparatus obtains three-dimensional image data formed from a plurality of tomograms, as shown in FIG. 14. Referring to FIG. 14, T1 to Tn are two-dimensional tomograms of the macular portion. In the tomogram Tn, L1 is the boundary (to be referred to as an ILM boundary) between the inner limiting membrane and the overlying tissue. L2 is the boundary (to be referred to as an NFL boundary) between the nerve fiber layer and the underlying layer. L2' is the nerve fiber layer (to be referred to as NFL). L3 is the boundary (to be referred to as an IPL boundary) between the inner plexiform layer and the underlying layer. L4 is the boundary (to be referred to as an OPL boundary) between the outer plexiform layer and the underlying layer. L5 is the boundary (to be referred to as an IS/OS boundary) between the junction between the inner and outer segments of the photoreceptor cell and the overlying layer. L6 is the boundary (to be referred to as an RPE boundary) between the retinal pigment epithelium and the underlying layer.

Making an image diagnosis using the OCT apparatus requires a technique for specifying the boundary of each retina layer by image analysis. For example, if the ILM boundary L1 and NFL boundary L2 in FIG. 14 can be specified to measure the thickness of the NFL, the thickness can be used as one index for glaucoma diagnosis.

Various retina-layer, boundary-specifying algorithms have been proposed up to now. As a problem common to them, it becomes difficult to specify a retina-layer boundary upon a change of the layer structure owing to an artifact or lesion. For example, if a blood vessel or lesion exists in the retina layer, the luminance at a position deeper than the blood vessel or lesion drops or the retina layer locally swells. Only a single algorithm hardly specifies a retina-layer boundary. FIG. 15A exemplifies a tomogram in which a blood vessel V1 exists. FIG. 15B exemplifies a tomogram in which a hemorrhage B1 exists. FIG. 15C exemplifies a tomogram in which "detachment" of a vitreous cortex H1 and "cyst C1" exist. When the blood vessel V1 or hemorrhage B1 exists as shown in FIG. 15A or 15B, the luminance below it decreases, making it hard to see the boundary. In some cases, a lesion appears inside and outside the retina layer, as shown in FIG. 15C. In this case, no luminance decreases, but the entire retina layer swells or the originally existent retina-layer boundary is disconnected. When analyzing such a tomogram, an area where the layer structure has changed needs to be specified to switch processing to one optimum for changing the layer structure.

In Japanese Patent Laid-Open No. 2009-066015 (to be referred to as literature 1), statistical feature amounts above and below a pixel of interest are calculated in each A-scan, and it is determined that an artifact exists in an A-scan whose feature amount is equal to or smaller than a threshold. In Japanese Patent Laid-Open No. 2007-325831 (to be referred to as literature 2), a fundus image and tomogram are aligned, a blood vessel area extracted from the fundus image is projected onto the tomogram to specify the blood vessel position, and the blood vessel area within the tomogram undergoes different processing.

However, the conventional techniques have the following problems. The artifact specifying method in literature 1 considers that all artifacts arise from a blood vessel. This method does not discriminate an artifact caused by the blood vessel V1 as in FIG. 15A from one caused by the hemorrhage B1 as in FIG. 15B. Considering processing of interpolating a boundary within the artifact area, the same processing cannot be applied to an artifact caused by a blood vessel and an artifact caused by a hemorrhage because the range of the artifact area and the degree of change of the layer structure differ between these artifacts. The method in literature 2 switches processing by projecting, onto a tomogram, a blood vessel area extracted from a fundus image. Needless to say, this cannot be implemented unless a fundus image of the same patient as that of the tomogram is used. Further, this method cannot deal with a lesion which cannot be detected from a fundus image. There are lesions which hardly appear in a fundus image, such as detachment of the vitreous cortex H1 and the cyst C1 as shown in FIG. 15C. Hence, this method cannot cope with a lesion or the like which can be detected only from a tomogram.

SUMMARY OF THE INVENTION

One aspect of the present invention provides an image processing apparatus and method capable of specifying, from the tomogram of the retina, a cause of a change in the retina layer structure.

According to one aspect of the present invention, there is provided an image processing apparatus which processes a plurality of tomograms obtained by acquiring, along a direction crossing at a right angle a section along a thickness direction of a retina, a plurality of tomograms each including the section. The apparatus comprises: a detection unit configured to detect a layer structure in the retina from image information of respective lines of the tomograms along the thickness direction; an appending unit configured to append structure information to the respective lines based on the layer structures detected for the respective lines; and a mapping unit configured to map the structure information of the respective lines of the plurality of tomograms onto a plane crossing the thickness direction at a right angle, thereby generating a two-dimensional image based on the structure information.

Furthermore, according to another aspect of the present invention there is provided an image processing method in an image processing apparatus which processes a plurality of tomograms obtained by acquiring, along a direction crossing at a right angle a section along a thickness direction of a retina, a plurality of tomograms each including the section. The method comprises a: detection step of detecting a layer structure in the retina from image information of respective lines of the tomograms along the thickness direction; an appending step of appending structure information to the respective lines based on the layer structures detected in the detection step; and a mapping step of mapping the structure information of the respective lines of the plurality of tomograms onto a plane crossing the thickness direction at a right angle, thereby generating a two-dimensional image based on the structure information.

Further features of the present invention will become apparent from the following description of exemplary embodiments with reference to the attached drawings.

DESCRIPTION OF THE EMBODIMENTS

First Embodiment

Figure 14:
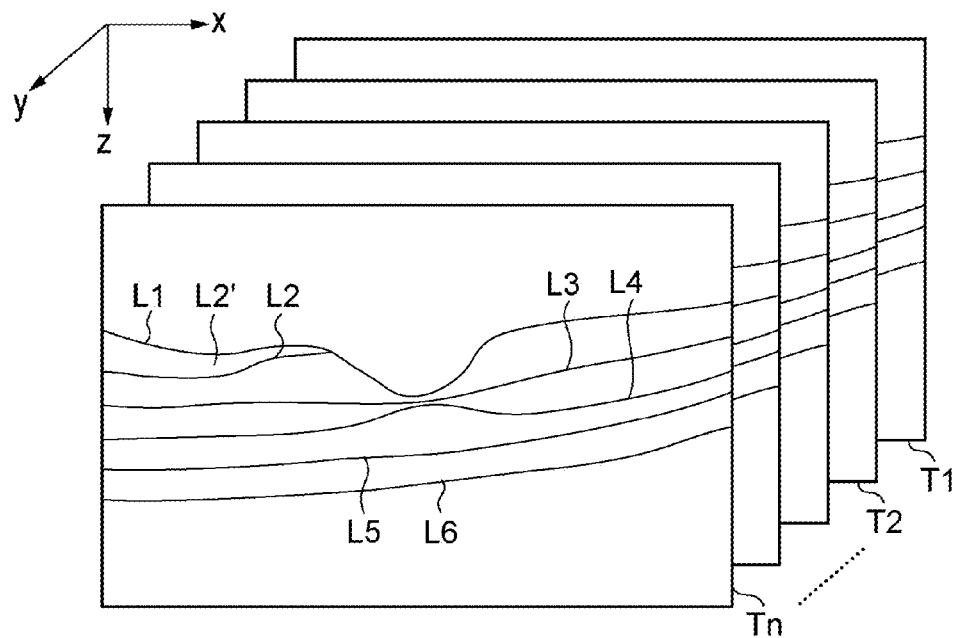
FIG. 14 is a schematic view showing tomograms of the macular portion.
Figure 15A:
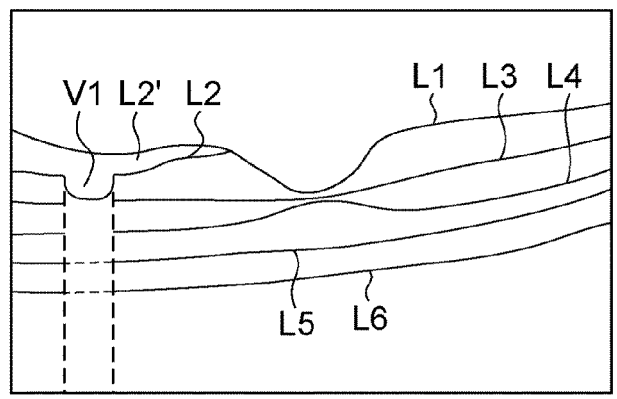
FIGS. 15A to 15C are schematic views showing tomograms of the macular portion including artifact areas caused by a blood vessel and hemorrhage.
Figure 15B:
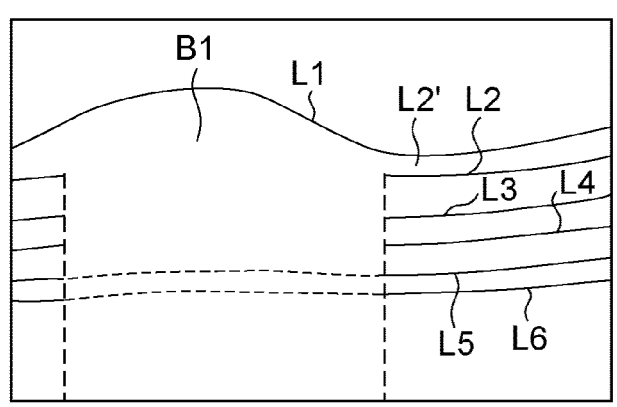
Figure 15C:
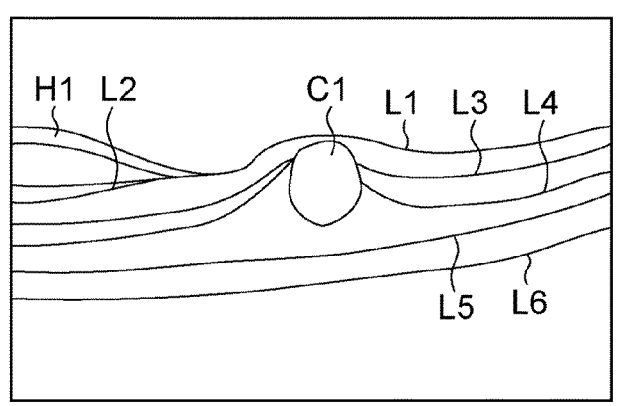

The configuration of a tomogram imaging system according to the first embodiment will be described with reference to FIG. 1. In the tomogram imaging system of the first embodiment, a tomogram acquisition apparatus 20 acquires a tomogram of an eye to be examined. An image processing apparatus 10 analyzes each A-scan of the tomogram acquired by the tomogram acquisition apparatus 20, and acquires information about the retina layer structure (to be referred to as structure information). The image processing apparatus 10 then maps the acquired structure information on a two-dimensional map of the x-y plane in FIG. 14. The image processing apparatus 10 analyzes the structure information-mapped two-dimensional map, and specifies a lesion or structure which changes the retina layer structure.

The image processing apparatus 10 is communicably connected to the tomogram acquisition apparatus 20 and a save unit 30. The tomogram acquisition apparatus 20 acquires, from an instruction acquisition unit 21, instruction information input by an operator (not shown). The tomogram acquisition apparatus 20 images an eye to be examined in accordance with the acquired instruction information, and transmits the obtained image to the image processing apparatus 10 and save unit 30.

The tomogram acquisition apparatus 20 is, for example, an OCT imaging apparatus using OCT (Optical Coherence Tomography) to be described later with reference to FIG. 3. The OCT imaging apparatus generates interference light from reflected light and scattered light (return light) by an object irradiated with signal light, and reflected light of reference light emitted to a reference object. The OCT imaging apparatus analyzes the interference light to image the internal structure of the object (internal structure of the retina). When the object has a layer structure, the image of the layer structure can be formed based on the intensity of return light serving as light reflected or scattered by each layer. The OCT imaging apparatus irradiates a predetermined point on the retina with signal light, obtaining information (to be referred to as an A-scan) in the depth direction (z direction in FIG. 14) at the point. More specifically, the A-scan obtains image information of the retina along the thickness direction. A-scans are executed at a predetermined interval on a predetermined line on the retina surface and are integrated, acquiring a tomogram (to be referred to as a B-scan) along the thickness direction of the retina (for example, an image of the x-z plane in FIG. 14). A plurality of tomograms can be acquired by performing A-scans in a predetermined range on the retina surface. Further, these tomograms can be reconstructed into three-dimensional volume data. For example, a plurality of tomograms (B-scans) are acquired (to be referred to as a C-scan) in a direction crossing at a right angle a section along the thickness direction of the retina, acquiring a plurality of B-scans. These B-scans can be reconstructed into three-dimensional volume data. Accordingly, even a retina image at an arbitrary depth can be acquired (image of the x-y plane in FIG. 14).

Figure 1:
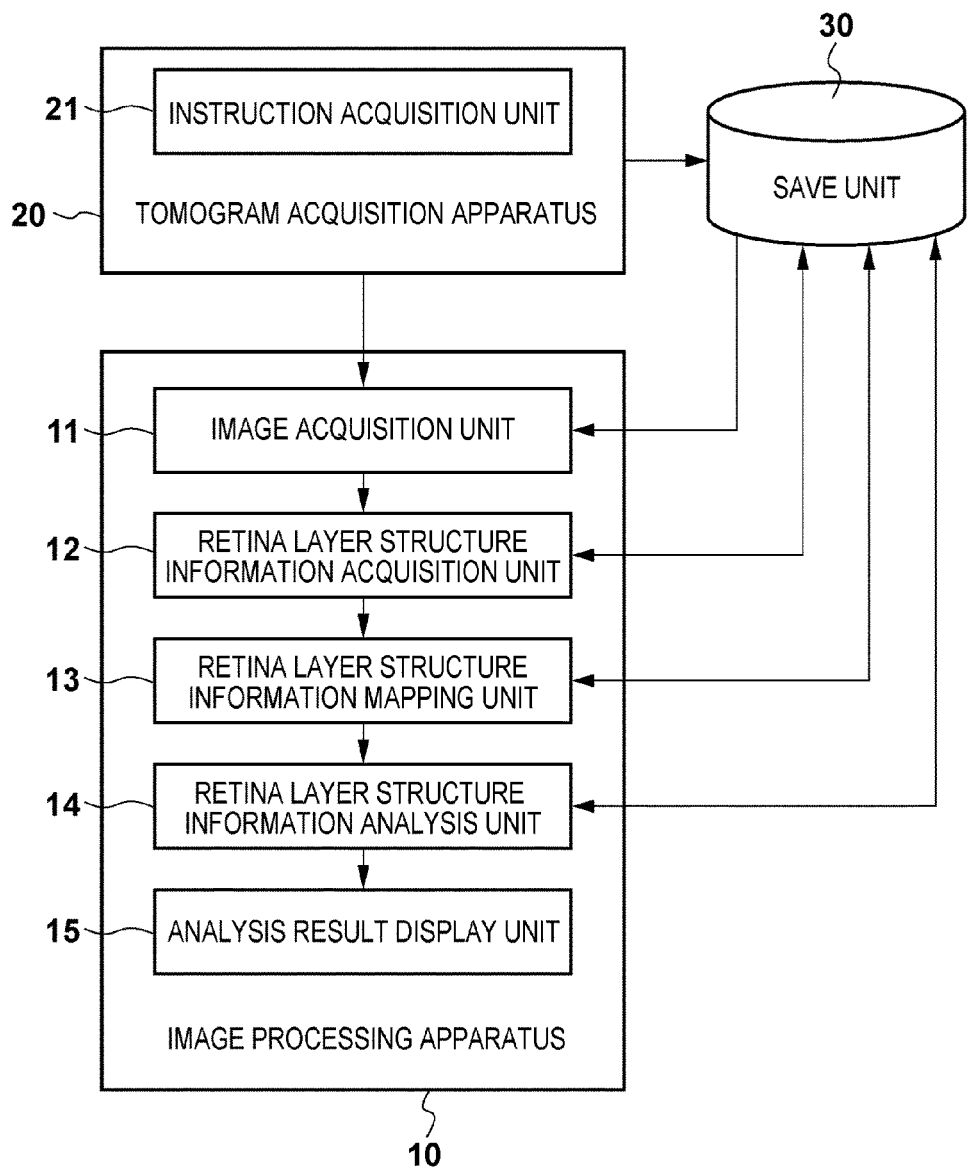
FIG. 1 is a block diagram exemplifying the functional configuration of an image processing system.

The image processing apparatus 10 includes, for example, respective blocks shown in FIG. 1 as circuits. As another example, the image processing apparatus 10 is formed from a well-known computer, and implements functions corresponding to the respective blocks by cooperation between hardware and software. The computer includes, for example, a CPU, ROM, RAM, a HDD, a mouse, a keyboard, a network I/F, and a display unit. In this case, the ROM or HDD stores a program for providing the functions shown in FIG. 1 in cooperation with the respective hardware components of the image processing apparatus 10 and implementing processing shown in FIG. 4 (to be described later). This program is expanded in the RAM, and the CPU executes the instruction, providing the functions shown in FIG. 1 and implementing the processing shown in FIG. 4.

The respective functions of the image processing apparatus 10 will be explained. An image acquisition unit 11 acquires a tomographic image from the tomogram acquisition apparatus 20. A retina layer structure information acquisition unit 12, a retina layer structure information mapping unit 13, and a retina layer structure information analysis unit 14 perform predetermined processes for the image acquired by the image acquisition unit 11. After specifying a blood vessel or lesion, an analysis result display unit 15 formed from a liquid crystal display or the like displays the image. The retina layer structure information acquisition unit 12, the retina layer structure information mapping unit 13, the retina layer structure information analysis unit 14, and the analysis result display unit 15 will be referred to as the structure acquisition unit 12, the mapping unit 13, the analysis unit 14, and the display unit 15, respectively.

Figure 2:
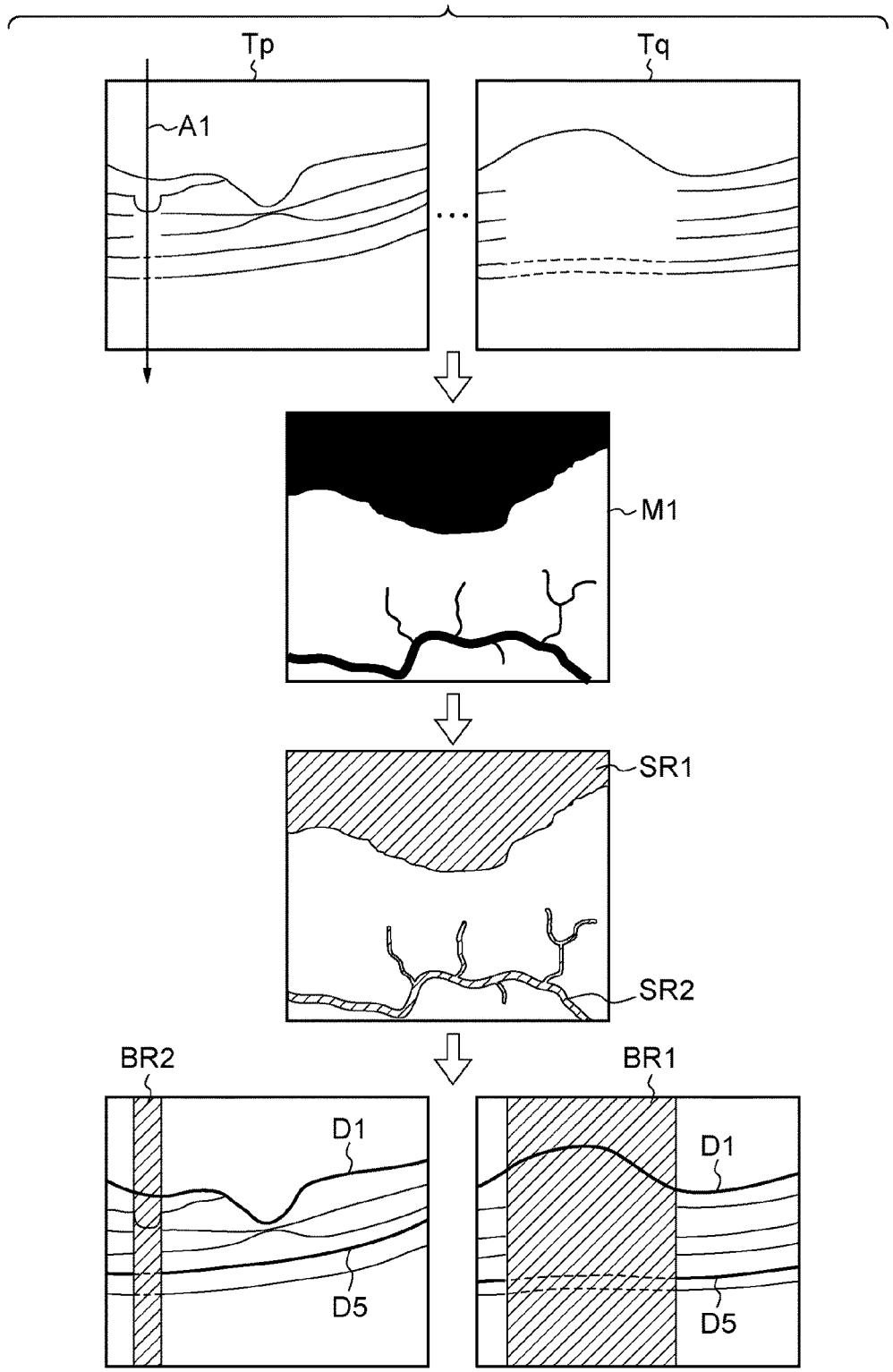
FIG. 2 is a view showing an outline of processing by the image processing system.

An outline of the embodiment will be explained with reference to FIG. 2. Referring to FIG. 2, Tp to Tq are tomograms acquired by the tomogram acquisition apparatus. First, a tomogram is scanned in the A-scan direction A1 to acquire structure information from image information of the retina layer in the A-scan direction. The structure information is mapped in a two-dimensional map M1 of a plane perpendicular to the A-scan direction. The two-dimensional map M1 in FIG. 2 is an example of mapping A-scans containing artifacts, details of which will be described later. Then, artifact-containing areas formed on the two-dimensional map M1 are analyzed, and the respective areas are classified into a structure and lesion present in the retina layer. An area SR1 in FIG. 2 is classified into an artifact caused by a hemorrhage, and an area SR2 is classified as an artifact caused by a blood vessel. Finally, specified retina-layer-structure information including a hemorrhage-artifact area BR1, blood-vessel-artifact area BR2, retina-layer boundary D1 (ILM boundary), and IS/OS boundary D5 obtained by the analysis is superimposed and displayed on the image.

Figure 3:
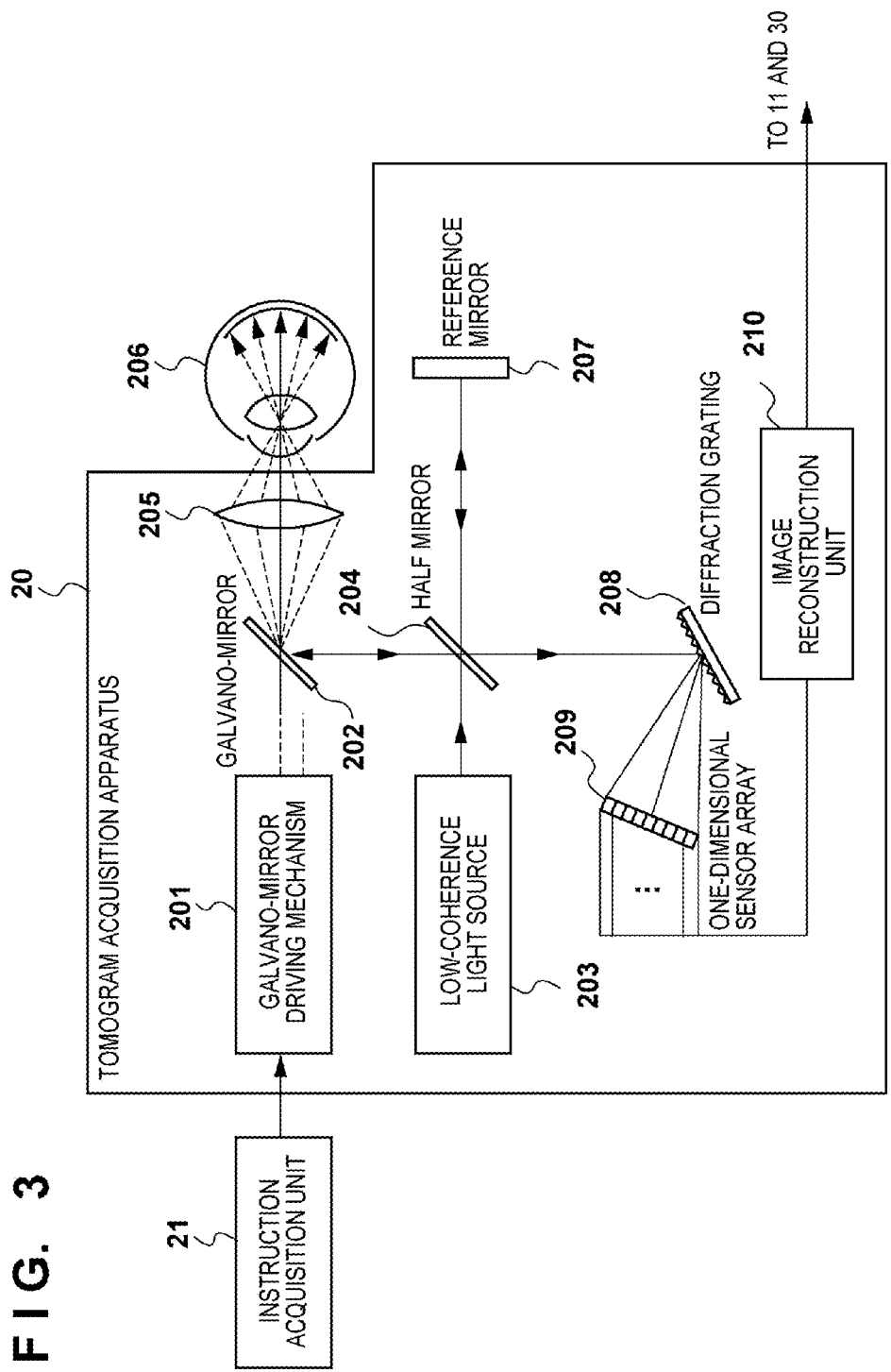
FIG. 3 is a view exemplifying the arrangement of a tomogram acquisition apparatus 20.

FIG. 3 shows the functional arrangement of the tomogram acquisition apparatus 20. The instruction acquisition unit 21 acquires instruction information to adjust the two-dimensional measurement range and the measurement depth for the fundus of an eye to be examined. The tomogram acquisition apparatus 20 controls a galvano-mirror driving mechanism 201 to drive a galvano-mirror 202 using the instruction information as an imaging parameter. A half mirror 204 splits a light beam emitted by a low-coherence light source 203 into signal light directed toward an eye 206 to be examined via an objective lens 205 and reference light directed toward a reference mirror 207 arranged permanently. The half mirror 204 superimposes the signal light reflected by the eye 206 to be examined and the reference light reflected by the reference mirror 207, generating interference light. A diffraction grating 208 splits the interference light into wavelength components of wavelengths $\lambda 1$ to $\lambda n$. A one-dimensional photosensor array 209 detects beams of the wavelength components split by the diffraction grating 208. Respective photosensors which form the one-dimensional photosensor array 209 output detection signals of the light intensities of the detected wavelength components to an image reconstruction unit 210.

The image reconstruction unit 210 obtains the relationship between the wavelength and light intensity of the interference light, that is, the light intensity distribution (wavelength spectrum) of the interference light, based on the detection signals of the wavelength components of the interference light that are output from the one-dimensional photosensor array 209. The image reconstruction unit 210 Fourier-transforms the obtained wavelength spectrum of the interference light, reconstructing the tomogram of the retina.

Figure 4:
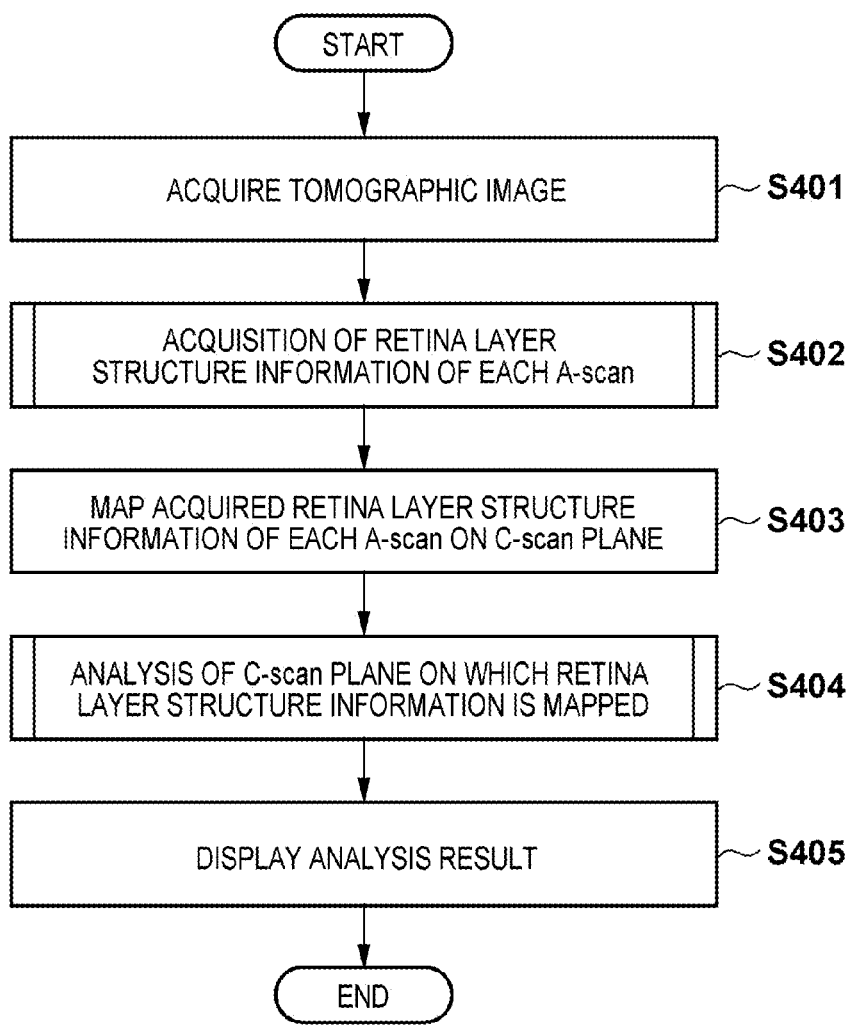
FIG. 4 is a flowchart showing a processing sequence by an image processing apparatus 10 according to the first embodiment.

FIG. 4 is a flowchart of the embodiment. A detailed processing sequence to be executed by the image processing apparatus 10 will be explained with reference to the flowchart.

In step S401, the image acquisition unit 11 acquires an OCT tomogram imaged by the tomogram acquisition apparatus 20.

In step S402, the structure acquisition unit 12 acquires structure information from each A-scan in the OCT tomogram acquired in step S401. In the embodiment, "ILM", "IS/OS", "position of a vitreous-cortex candidate", and "presence/absence of an artifact" are detected for each A-scan. Based on these pieces of information, structure information is generated. In the embodiment, the boundary position of a predetermined layer in the retina is detected based on image information of a line of a tomogram by a B-scan along the thickness direction (line along an A-scan), and is used as structure information. In the embodiment, an artifact attribute representing that an artifact exists is appended to a line on which no predetermined layer has been detected. Further, an artifact attribute representing that no artifact exists is appended to a line on which the predetermined layer has been detected. The embodiment uses the IS/OS boundary as the boundary of the predetermined layer used to determine the presence/absence of an artifact. An artifact attribute (label) indicating the presence of an artifact is appended to a line on which no IS/OS boundary has been detected. However, the boundary of a layer used to detect an artifact is not limited to one described in the embodiment. When acquiring structure information, a median filter and Sobel filter are applied to a tomogram, creating images (to be referred to as a median image and Sobel image). Profiles are created for each A-scan from the converted median image and Sobel image. Then, a peak in the profile created from the Sobel image is detected. Structure information is acquired by referring to a profile of the median image that corresponds to the vicinity of the detected peak or the interval between peaks. Details of processing for acquiring structure information will be described later with reference to FIG. 5.

Figure 9:
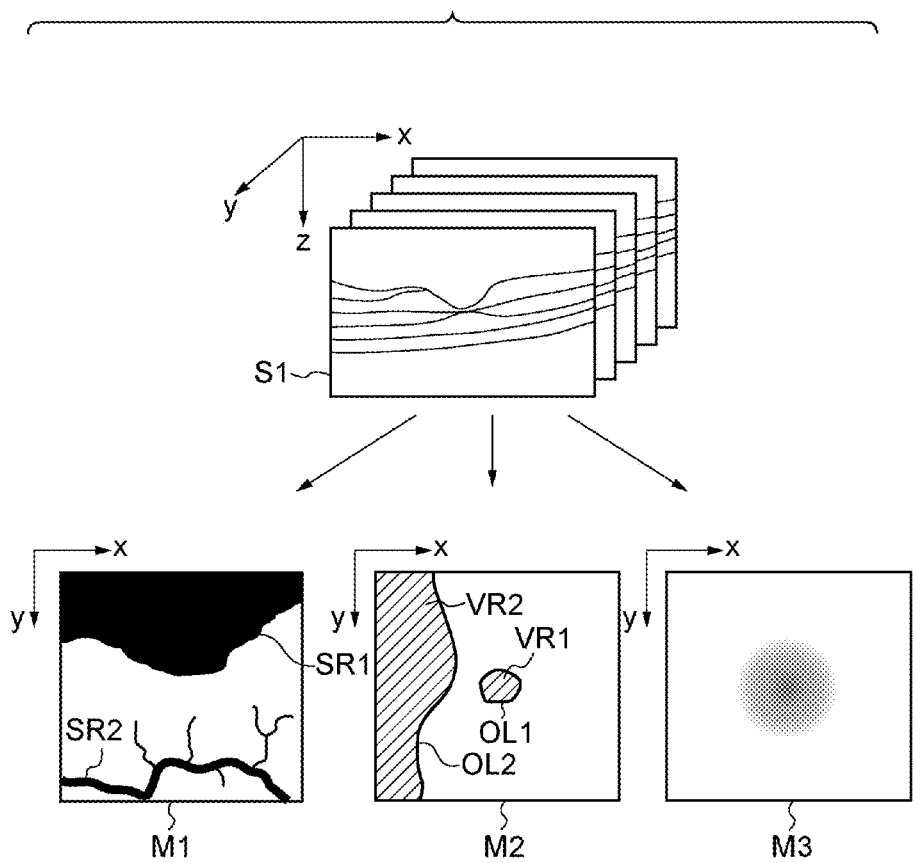
FIG. 9 is a view showing mapping of an A-scan containing an artifact in a map.

In step S403, the mapping unit 13 maps pieces of structure information of the respective A-scans acquired in step S402 on a two-dimensional map of the x-y plane (plane crossing the thickness direction of the retina at a right angle (c-scan plane)), as shown in FIG. 9. The two-dimensional map in which structure information is mapped will be called a structure-information map. In the embodiment, a structure-information map is created for each type of structure information, as shown in FIG. 9. More specifically, according to the present embodiment, pieces of structure information handled in the embodiment are "presence/absence of an artifact", "vitreous-cortex candidate", "ILM boundary", and "IS/OS boundary". Thus, four structure-information maps are created. A structure-information map M1 is created regarding "presence/absence of an artifact". This structure-information map represents in black an A-scan in which an artifact exists, and has areas SR1 and SR2 where artifacts exist.

A structure-information map M2 is created regarding "vitreous-cortex candidate". In addition to the presence/absence of vitreous-cortex candidates (areas VR1 and VR2 where vitreous-cortex candidates exist), the pieces of position information (z-coordinate values) are specified for each A-scan. Therefore, a structure-information map in which z-coordinate values are input is created. As for "mM boundary" and "IS/OS boundary", a structure-information map in which pieces of position information of the ILM boundary and IS/OS boundary specified for each A-scan are input is created, like a structure-information map M3. Note that the structure information is not limited to them. For example, a structure-information map in which the presence/absence of a white spot and its coordinate value are mapped for each A-scan may be created.

In step S404, the analysis unit 14 analyzes the structure information using the structure-information map created in step S403. In the embodiment, a lesion is specified and the result is corrected on the structure-information map by combining the sizes (areas) and/or shapes of the areas formed by structure information or a plurality of types of structure information. Particularly in the first embodiment, the type of artifact (for example, an artifact caused by a blood vessel or one caused by a hemorrhage) is determined based on the size or shape of an artifact area on the two-dimensional map M1 in which an artifact label is mapped. Detailed processing will be exemplified later with reference to FIG. 6.

Figure 13A:
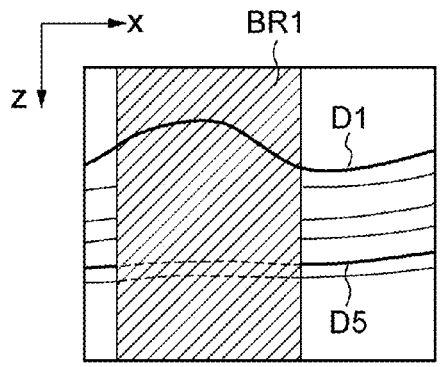
FIGS. 13A to 13E are views showing examples of superimposing and displaying analysis results on a C-scan plane and tomogram.
Figure 13B:
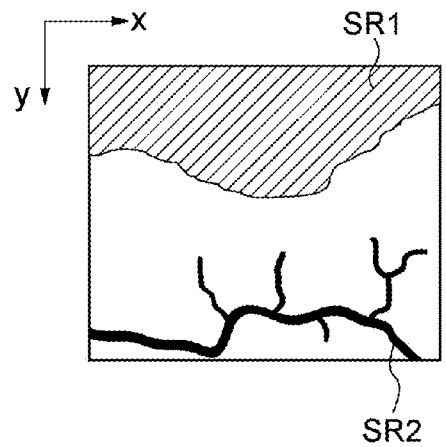

In step S405, the specified structure information is superimposed on a tomogram, an integrated image, or a fundus image if it exists. The display unit 15 displays the resultant image. In the embodiment, the specified retina-layer boundaries D1 and D5 are superimposed on a tomogram of a plane parallel to the z direction, as shown in FIG. 13A. The remaining structure information is superimposed on a tomogram of a plane parallel to the z direction or an integrated image of a plane perpendicular to the z direction. FIG. 13A shows a tomogram on which all pieces of specified structure information (ILM boundary D1, IS/OS boundary D5, and area BR1 where an artifact caused by a hemorrhage exists) are superimposed. FIG. 13B shows an integrated image on which pieces of structure information indicating the presence/absence of an artifact caused by a hemorrhage and the presence/absence of an artifact caused by a blood vessel are superimposed. A-scans with hemorrhage and blood vessel labels may be displayed in different colors so that they can be discriminated from other A-scans, like BR1 shown in FIG. 13A. In the integrated image of FIG. 13B, the area SR1 is a hemorrhage area, and the area SR2 is a blood vessel area. As shown in FIG. 13B, different structures (artifacts by different causes) such as a hemorrhage and a blood vessel may be displayed in different colors on the same plane so that the observer can recognize them.

In this manner, pieces of structure information acquired from respective A-scans are mapped on a two-dimensional map and analyzed in the entire retina layer area. This allows specifying the cause of an artifact and correcting structure information from only tomograms.

<Retina-Layer-Structure-Information Acquisition Processing>

Figure 5:
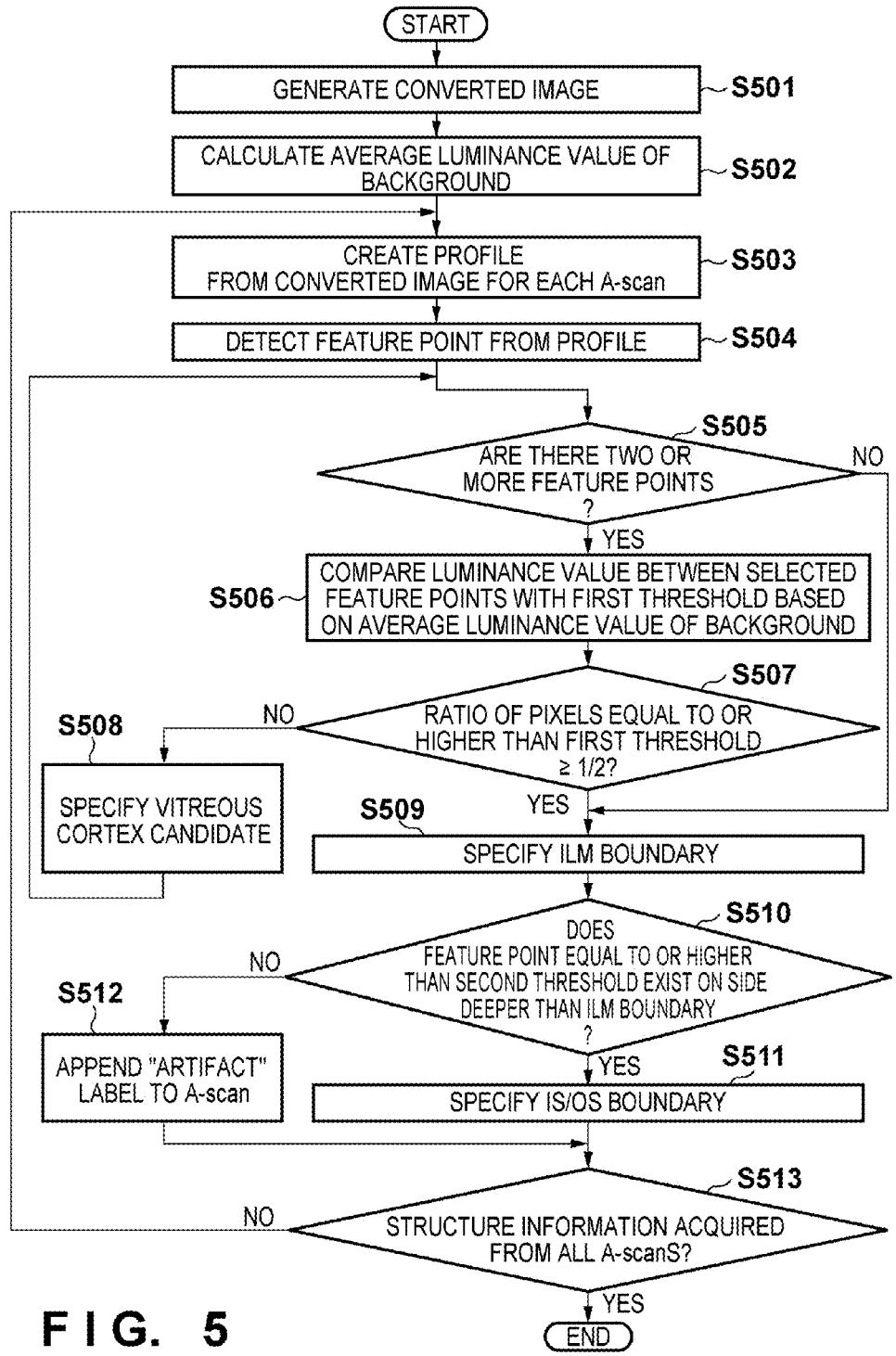
FIG. 5 is a flowchart showing a processing sequence by a retina layer structure information acquisition unit 12 according to the first embodiment.

Details of retina-layer-structure-information acquisition processing in step S402 will be explained with reference to FIG. 5. In step S501, the structure acquisition unit 12 converts an OCT tomogram acquired in step S401. In the embodiment, the median filter and Sobel filter are applied to the tomogram, creating a median image and a Sobel image. Assume that the pixel value becomes large for a high signal strength and small for a low signal strength.

In the embodiment, the Sobel filter has directivity to emphasize a boundary from a small luminance value to a large one when viewed from a shallow side in an A-scan (from above the image) because of the following reason. As structure information for specifying a cause when the retina layer structure changes, the embodiment uses the ILM boundary, IS/OS boundary, position information of the vitreous cortex, and the presence/absence of an artifact in each A-scan. In the retina layer structure, the ILM boundary and vitreous cortex serve as boundaries between the vitreous body, which has a small luminance value and the retina tissue, which has a relatively large luminance value. Even the IS/OS boundary contacts a relatively dark tissue on a shallow side. If an artifact exists, the luminance below the IS/OS boundary decreases. Hence, the presence/absence of an artifact can be determined from a pixel value in the Sobel image. That is, giving the above-mentioned directivity can further emphasize the ILM boundary, IS/OS boundary, and vitreous cortex, and even the presence/absence of an artifact can be determined. Note that the vitreous cortex is finally specified after retina-layer-structure-information acquisition processing and thus is handled as a vitreous-cortex candidate in retina-layer-structure-information acquisition processing.

In step S502, the structure acquisition unit 12 calculates the average luminance value of the background (vitreous body) using the median image created in step S501. In the embodiment, first, the median image undergoes binarization processing by a P-tile method to specify a background area. Then, the average value of the luminance value of the median image in the background area is calculated.

Binarization processing by the P-tile method is a method of creating the histogram of an image to be processed, accumulating luminance values from a large or small one, setting a luminance value obtained at a predetermined ratio P as a threshold, and performing binarization. In the embodiment, the ratio of a retina area in an image is roughly obtained. Binarization processing is done by empirically setting the P value to 30% in descending order of luminance value. Pixels whose luminance values are equal to or smaller than the threshold are determined as background pixels. After specifying background pixels, the average luminance value of the background is calculated by referring to the luminance value of the median image at the background pixels.

Figure 7:
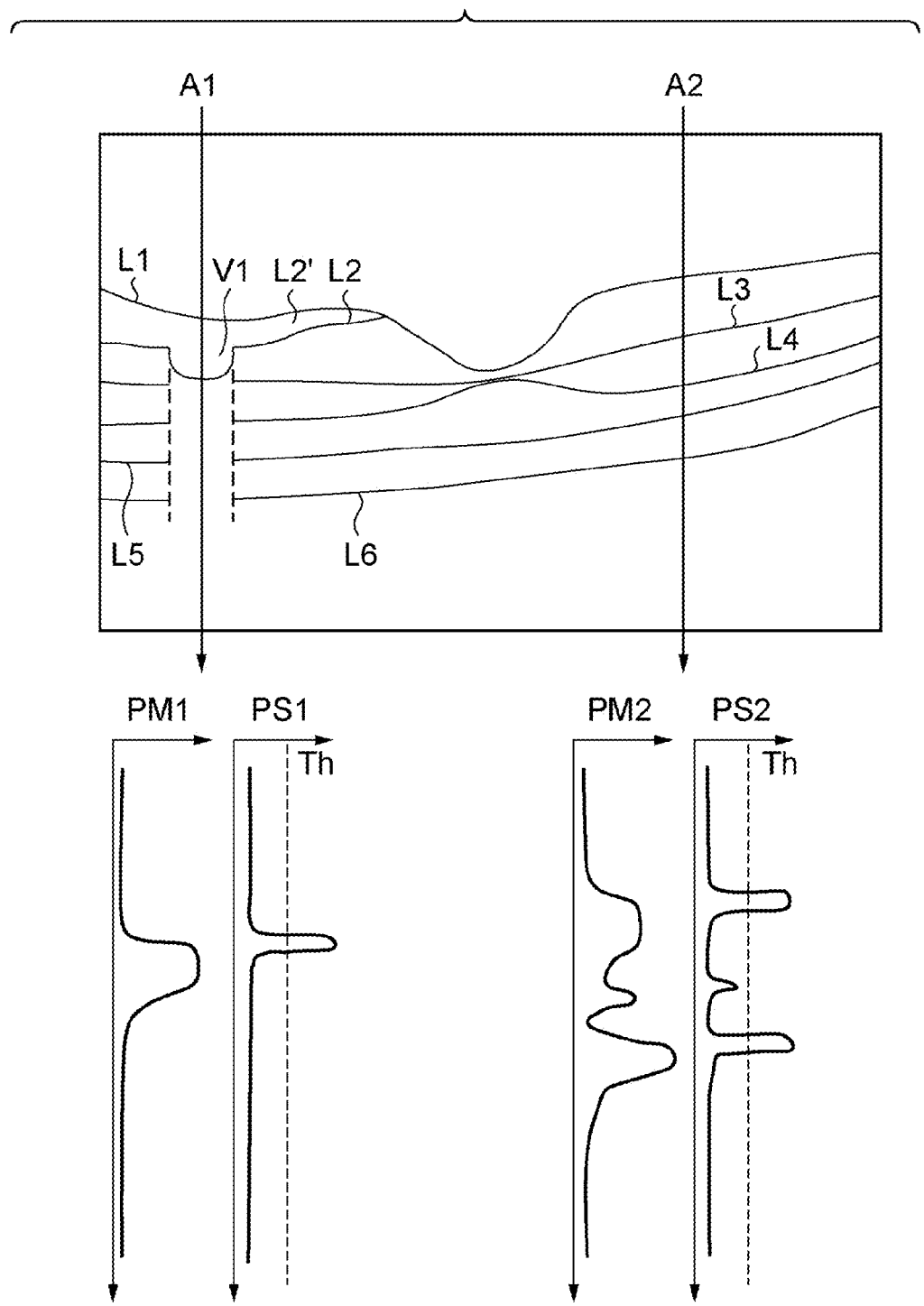
FIG. 7 is a view showing an A-scan profile in the tomogram of a macular portion.

In step S503, the structure acquisition unit 12 creates a profile from the converted image created in step S501. In the embodiment, profiles are created from both the median image and the Sobel image for each A-scan. Creating a profile from the median image has an effect of suppressing undesirable noise especially in an OCT image and more easily grasping the trend of the luminance value. Also, creating a profile from the Sobel image has an effect of easily detecting a candidate point of a retina-layer boundary when specifying a retina-layer boundary later. FIG. 7 shows profiles created from median images and Sobel images in A-scans A1 and A2 in a tomogram. As shown in FIG. 7, profiles PM1 and PM2 of the median images reveal the trend of the luminance value, and profiles PS1 and PS2 of the Sobel images represent candidate points of retina-layer boundaries. However, no profile need always be created from these converted images. It suffices to detect an edge having a predetermined intensity from an original image or another converted image.

In step S504, the structure acquisition unit 12 detects feature points from the profiles created in step S503. In the embodiment, local maximum points (to be referred to as peaks) in profiles (for example, PS1 and PS2) created from Sobel images are detected as feature points. The detection uses a threshold set empirically or based on image information. In the retina, many signals are reflected or scattered below the ILM boundary, below the IS/OS boundary, or by the vitreous cortex. For this reason, a boundary is easily detected as a strong edge using a Sobel filter having directivity to emphasize a boundary from a small luminance value to a large one when viewed from a shallow side, as described in step S501. A strong edge detected by the Sobel filter having such directivity is only a lesion other than the aforementioned layers. By adjusting the threshold, the ILM boundary, IS/OS boundary, and vitreous-cortex candidate can be extracted preferentially.

In step S505, the structure acquisition unit 12 counts peaks detected in step S504, and branches the process based on the count. In the embodiment, if there are two or more peaks which are specified neither as a retina-layer boundary nor as a vitreous-cortex candidate upon execution of step S504 (YES in step S505), two peaks are selected sequentially from a shallow side in the A-scan, and defined as the first and second peaks, respectively. The process then advances to step S506. If there is one peak (NO in step S505), the highest peak is defined as the first peak, and the process advances to step S509.

In step S506, the structure acquisition unit 12 compares the profile of the median image between the two peaks selected in step S505 with the first threshold based on the average luminance value of the background. In the embodiment, first, a value obtained by multiplying, by a coefficient of 1.2, the average luminance value of the background calculated in step S502 is set as the first threshold for pixels present between the first and second peaks. Then, the ratio of the number of pixels having luminance values larger than the first threshold to the total number of pixels present between the peaks is calculated. Note that this coefficient is obtained empirically, and the present invention is not limited to this. For example, the coefficient may be determined dynamically from image information using the ratio between the average luminance value of the background and that of an area (area equal to or larger than the threshold in binarization processing) other than the background.

In step S507, the structure acquisition unit 12 branches the process based on the ratio calculated in step S506. In the embodiment, if the calculated ratio is lower than ½ (NO in step S507), it is determined that the background exists between the peaks, and the process advances to step S508. If the calculated ratio is equal to or higher than ½ (YES in step S507), it is determined that the retina tissue exists between the peaks, and the process advances to step S509. Although which of the retina tissue and background exists is determined from the ratio of pixels equal to or larger than the threshold in the embodiment, the present invention is not limited to this. For example, it is also possible to calculate a feature amount from a profile and make a determination by an identification unit using the feature amount as an input.

In step S508, the structure acquisition unit 12 specifies one peak as a vitreous-cortex candidate. In the embodiment, as for the first and second peaks for which it is determined in step S507 that the background exists between the peaks, if the vitreous cortex is detached, the background exists below, and thus the first peak is specified as a vitreous-cortex candidate. After that, the process returns to step S505, and the next two peaks including the second peak are selected again.

In step S509, the structure acquisition unit 12 specifies one peak as the ILM boundary D1. In the embodiment, as for the first and second peaks for which it is determined in step S507 that the retina tissue exists between the peaks, the ILM boundary exists at the upper end of the retina tissue, so the first peak is specified as the ILM boundary. Even when the process branches from step S505, the first peak is specified as the ILM boundary.

In step S510, the structure acquisition unit 12 checks whether a feature point equal to or larger than the second threshold exists on a side (lower portion of the image) deeper than the ILM boundary specified in step S509 on the same A-scan. In the embodiment, a value obtained by multiplying, by a coefficient of 0.8, the magnitude of the peak of the ILM boundary specified on the same A-scan is set as the second threshold. It is checked whether a peak equal to or larger than the second threshold exists on a side deeper than the ILM boundary. If such a peak exists (YES in step S510), the process advances to step S511. If no such peak exists (NO in step S510), the process advances to step S512. Note that this threshold is obtained empirically, and the present invention is not limited to this. For example, the distance between peaks is also available other than the magnitude of the peak.

In step S511, the structure acquisition unit 12 specifies, as the IS/OS boundary, a peak equal to or higher than the second threshold that has been set in step S510. If there are a plurality of peaks equal to or higher than the second threshold, a peak at the shallowest position among the peaks equal to or higher than the second threshold is set as the IS/OS boundary in the embodiment. To the contrary, in step S512, the structure acquisition unit 12 determines that no IS/OS boundary has been specified, and appends the "artifact" label to the A-scan to represent the presence of an artifact.

In step S513, the structure acquisition unit 12 checks whether structure information has been acquired from all A-scans in the image. If all A-scans have been processed (YES in step S513), the process ends. If there is an A-scan whose structure information has not been acquired yet (NO in step S513), the process returns to step S503.

Figure 8A:
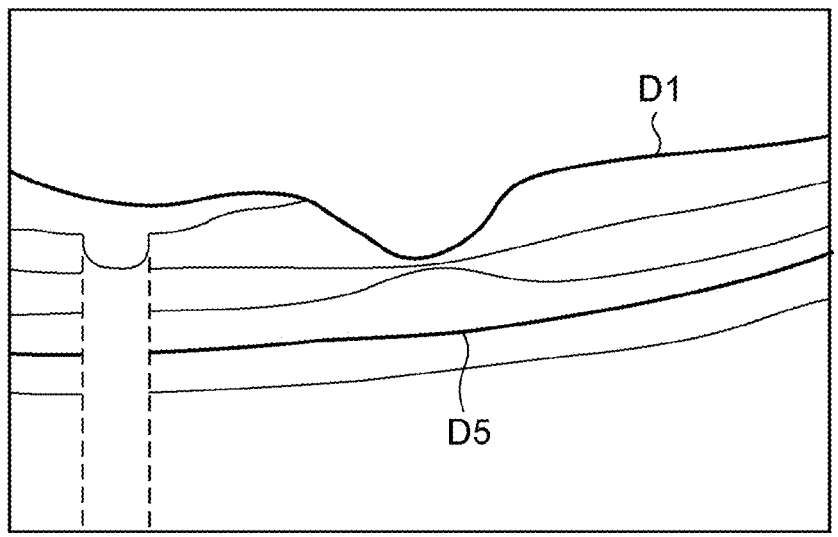
FIGS. 8A and 8B are views showing the ILM boundary and IS/OS boundary specified in tomograms containing a blood vessel and hemorrhage.
Figure 8B:
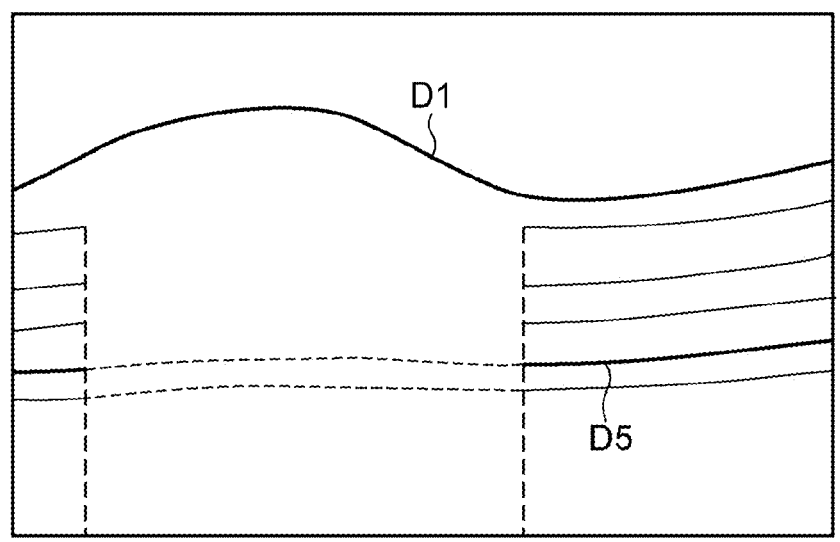

In this fashion, a tissue between peaks is determined, and structure information of the retina layer is acquired based on the result. This can reduce the structure information error. FIGS. 8A and 8B show tomograms in which the ILM boundary and IS/OS boundary are specified using this method. D1 and D5 indicated by thick solid lines in FIGS. 8A and 8B are the specified ILM boundary and IS/OS boundary, respectively. As can be seen from FIGS. 8A and 8B, the ILM boundary is specified in all A-scans. In contrast, the IS/OS boundary cannot be specified in some A-scans, and the "artifact" label is appended to these A-scans, as described in step S512. For example, the "artifact" label is appended to the A-scan A1 in FIG. 7.

<Retina-Layer-Structure-Information Analysis Processing>

Figure 6:
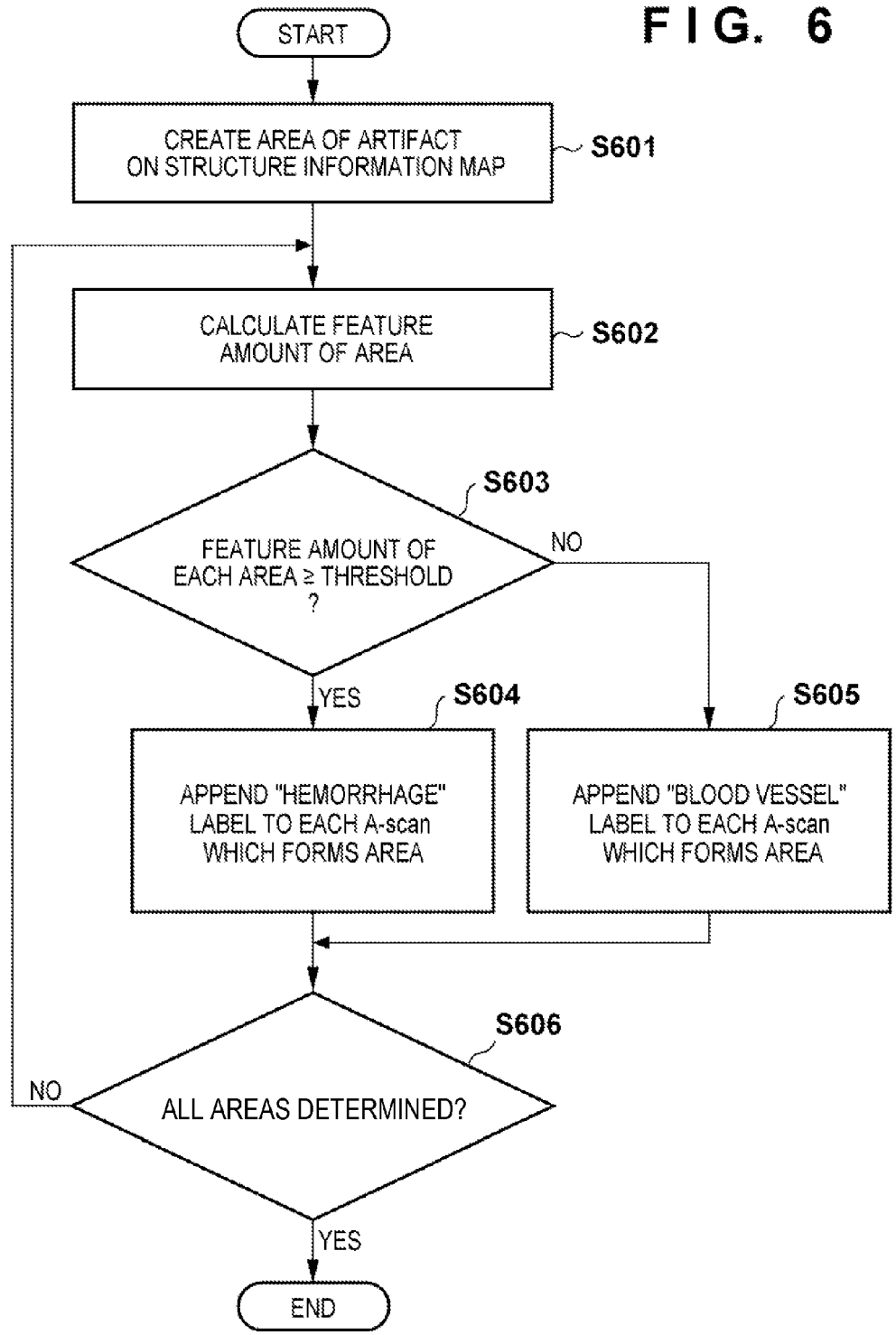
FIG. 6 is a flowchart showing a processing sequence by a retina layer structure information analysis unit 14 according to the first embodiment.

Details of retina-layer-structure-information analysis processing in step S404 will be explained with reference to FIG. 6.

In step S601, the analysis unit 14 creates an area on the structure-information map created in step S403. In the embodiment, an area is formed from artifact label-appended A-scans on the structure-information map M1 of FIG. 9. The two areas SR1 and SR2 are formed on the structure-information map M1 of FIG. 9.

In step S602, the analysis unit 14 calculates a feature amount for each area created in step S601. In the embodiment, the area of each area, and a rectangle passing through the maximum and minimum values of the x-coordinate of each area and those of the y-coordinate (that is, a rectangle circumscribing the area) are prepared. The ratio of an artifact area to the rectangle area (to be referred to as filling factor) is calculated as a feature amount. These parameters indicate a "plane likelihood" or a "line likelihood" of an artifact area, and are used to determine which of a hemorrhage and blood vessel is the factor of an area determined as an artifact area, which will be described later. Note that the calculated feature amount is not limited to them. For example, the line likelihood or plane likelihood of an area may be calculated as a feature amount using distance transform.

In step S603, by using the feature amount calculated in step S602, the analysis unit 14 determines which of a blood vessel and hemorrhage generates each artifact area. In the embodiment, a threshold is set for each feature amount. If the area of each area is equal to or larger than a predetermined value and the filling factor is equal to or higher than a predetermined value (YES in step S603), the area is regarded as an artifact area caused by a hemorrhage, and the process advances to step S604; otherwise (NO in step S603), the area is regarded as an artifact area caused by a blood vessel, and the process advances to step S605. On the structure-information map M1 of FIG. 9, the area SR1 is determined as an artifact area caused by a hemorrhage, and SR2 is determined as an artifact area caused by a blood vessel. Note that the artifact-area-type determination method is not limited to this. For example, an identification unit may make a determination using a predetermined feature amount as an input.

In step S604, the analysis unit 14 appends the "hemorrhage" label to each A-scan of an area determined in step S603 to contain an artifact caused by a hemorrhage. On the structure-information map M1 of FIG. 9, the "hemorrhage" label is appended to each A-scan forming the area SR1. To the contrary, in step S605, the analysis unit 14 appends the "blood vessel" label to each A-scan of an area determined in step S603 to contain an artifact caused by a blood vessel. On the structure-information map M1 of FIG. 9, the "blood vessel" label is appended to each A-scan forming the area SR2.

In step S606, the analysis unit 14 checks whether an area which has not been determined in step S603 exists among the areas of artifacts on the structure-information map. If all areas have been determined (YES in step S606), the process ends. If an undetermined area exists (NO in step S606), the process returns to step S602 to perform determination processing for an undetermined area.

As described above, according to the first embodiment, a retina layer structure can be analyzed on the map to check the shape of an artifact area when viewed from the entire retina layer. Even the cause of the artifact can be specified.

Second Embodiment

Figure 11:
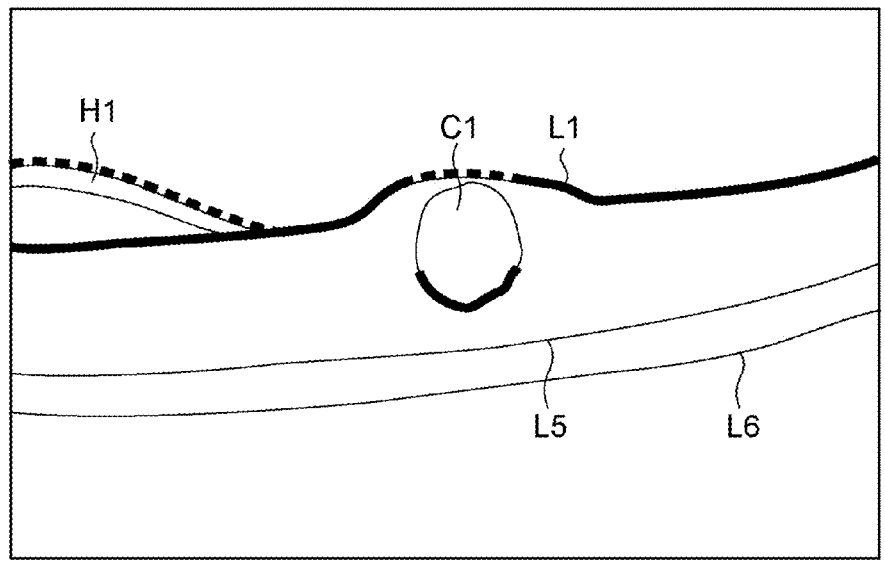
FIG. 11 is a schematic view showing the tomogram of the macular portion containing the vitreous cortex and a cyst.

The second embodiment will describe an example in which the vitreous cortex and a cyst are specified and the ILM boundary is corrected in step S404 of the first embodiment. In a tomogram, a detached vitreous cortex H1 may float above the ILM boundary L1, as shown in FIG. 11. Also, a lesion called "cyst" which forms a hole in the retina layer sometimes appears, like C1 in FIG. 11. If such a tomogram undergoes retina-layer-structure-information acquisition processing as in the first embodiment, the vitreous-cortex candidate H1 is indicated by a dotted line, and the ILM boundary L1 is indicated by a thick solid line, as shown in FIG. 11. This recognition error arises because the average luminance value of the cyst area is very close to the background (vitreous body). Hence, the original ILM boundary is recognized as a vitreous-cortex candidate, and a boundary below the cyst is recognized as the ILM boundary, as shown in FIG. 11. To prevent this, the second embodiment executes vitreous-cortex-specifying processing, cyst-specifying processing, and ILM-boundary-correction processing using a structure-information map to be described later, instead of or in addition to analysis processing in FIG. 6. Even in a tomogram as shown in FIG. 11, the vitreous cortex, cyst, and ILM boundary can be specified without a recognition error.

Figure 10:
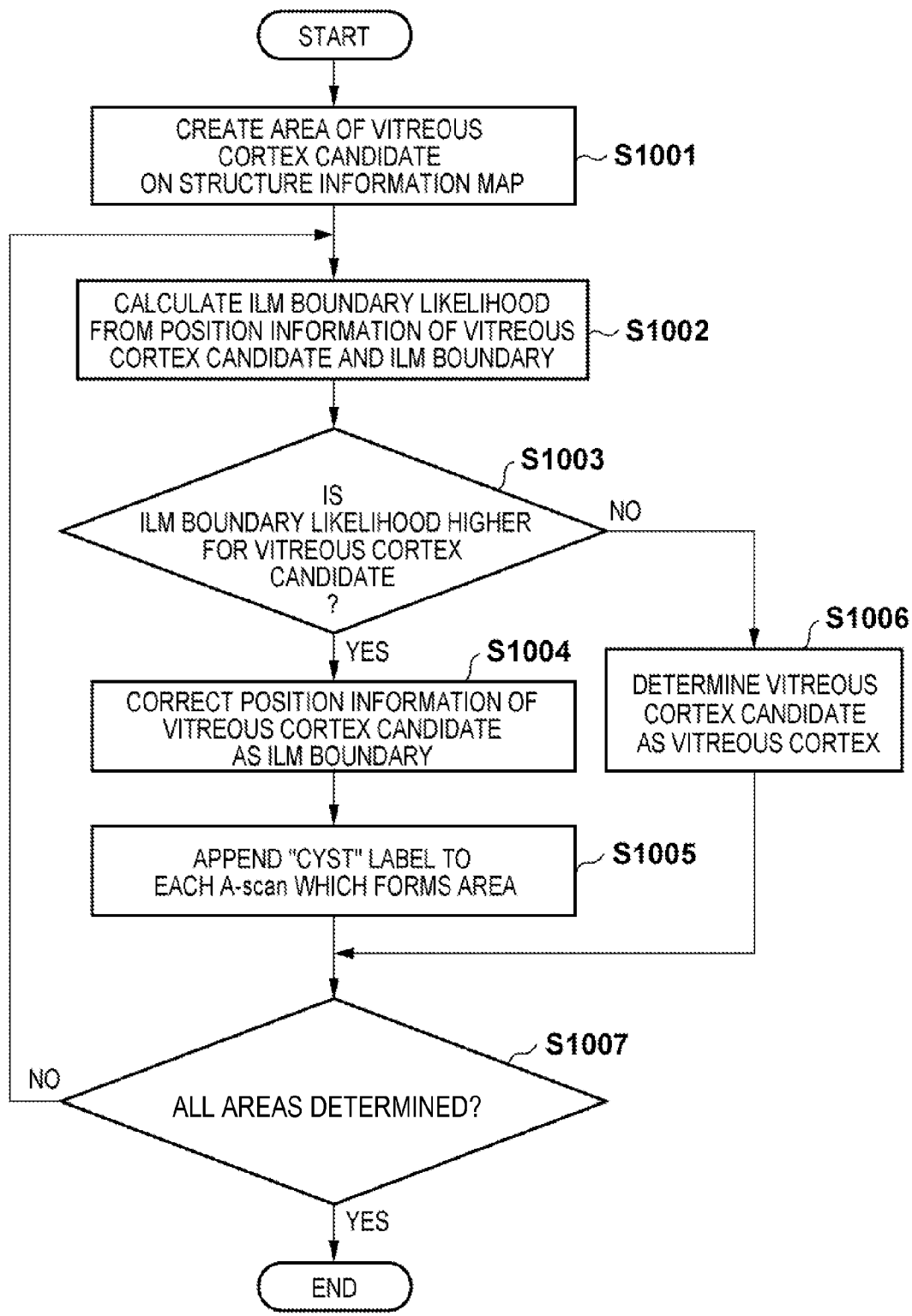
FIG. 10 is a flowchart showing a processing sequence by a retina layer structure information analysis unit 14 according to the second embodiment.

The second embodiment is the same as the first embodiment except for retina-layer-structure-information analysis processing. As for the apparatus arrangement, the second embodiment is the same as the first embodiment except that when an image processing apparatus 10 operates based on a software instruction, a program stored in a ROM or HDD executes processing shown in FIG. 10 and implements functions for it. Details of retina-layer-structure-information analysis processing in step S404 according to the second embodiment will be explained with reference to FIG. 10.

Figure 12:
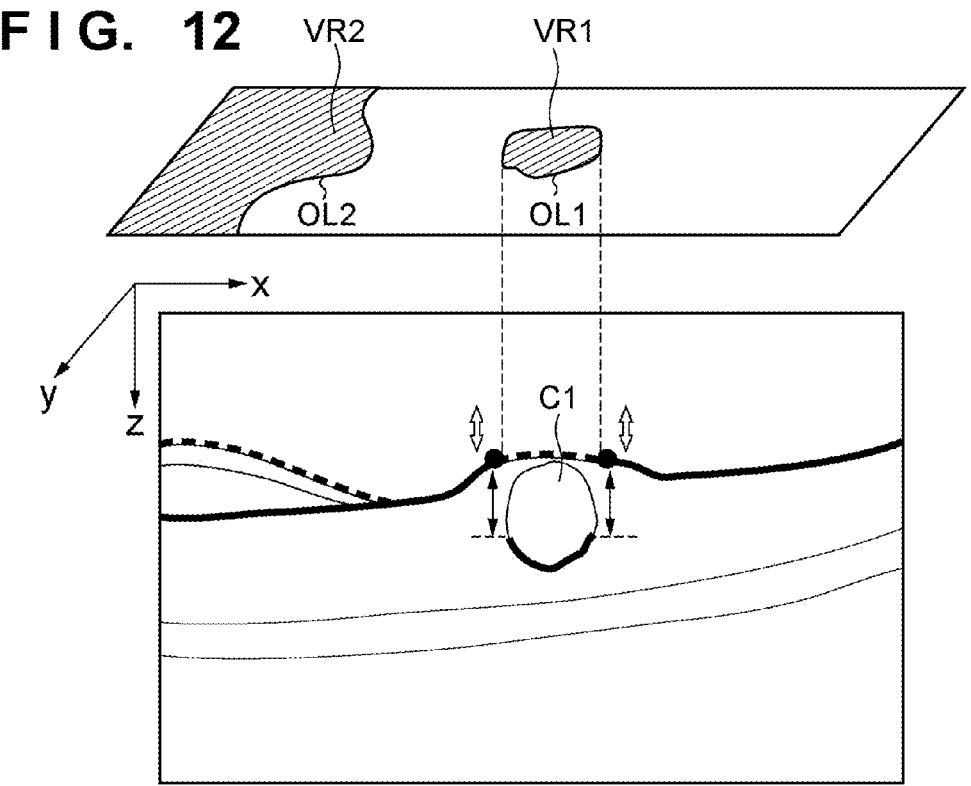
FIG. 12 is a view showing ILM boundary correction processing using a structure-information map.

In the second embodiment, image information of a line along the thickness direction of a tomogram is analyzed to detect a line on which the boundaries of the first and second layers are separated. The separation-detected line is mapped on a plane crossing the thickness direction at a right angle, generating a two-dimensional map. If it is determined that the second layer is discontinuous in the thickness direction at the boundary of an area where the separation-detected line is mapped on the plane, a position determined to be the boundary of the first layer is corrected to the boundary of the second layer in this area. The embodiment uses the vitreous cortex as the boundary of the first layer and the ILM boundary as the boundary of the second layer. Based on the determination of a discontinuity, the presence of a cyst in the retina is detected. First in step S1001, an analysis unit 14 creates an area on a structure-information map created in step S403. The embodiment uses a vitreous-cortex-candidate, structure-information map M2 (FIG. 9). FIG. 12 is a view showing the association between the structure-information map M2 in FIG. 9 and a B-scan image. Retina-layer-structure-analysis processing in the second embodiment will be described by exemplifying a case in which the structure-information map M2 having areas VR1 and VR2 where vitreous-cortex candidates are detected is obtained.

In step S1002, the analysis unit 14 checks a connection with the neighboring ILM boundary in the vitreous-cortex-candidate area created in step S1001, and calculates the index (to be referred to as an ILM boundary likelihood). In the embodiment, ILM boundary likelihoods are calculated and compared for a vitreous-cortex-candidate position and ILM-boundary position on the outlines (OL1 and OL2 in FIGS. 9 and 12) of the vitreous-cortex-candidate areas VR1 and VR2. Note that the areas VR1 and VR2 where vitreous-cortex candidates exist are obtained by mapping A-scans containing vitreous-cortex candidates onto the x-y plane. An area where a vitreous-cortex candidate exists is regarded as an area where the vitreous cortex and ILM boundary are separated.

Calculation of the ILM boundary likelihood will be explained in detail. First, the ILM boundary position of an A-scan, which is outside the outline of a vitreous-cortex-candidate area and does not have a vitreous-cortex candidate, is set as a reference, as shown in FIG. 12. Then, the absolute value of the difference (difference in the z-coordinate) between the reference position and a vitreous-cortex-candidate position in an A-scan of the outline, and the absolute value of the difference (difference in the z-coordinate) between the reference position and an ILM-boundary position in the A-scan of the outline are calculated. Respective absolute values are calculated and added for A-scans which form the outline. As the thus-obtained sum of z-coordinate differences is smaller, the ILM boundary likelihood is considered to be higher and the boundary is highly likely to be the ILM boundary (in actual calculation, a value obtained by multiplying the sum of z-coordinate differences by −1 is set as the ILM boundary likelihood). As a result, the ILM likelihoods at the vitreous-cortex candidates of the vitreous-cortex-candidate areas VR1 and VR2, and the ILM likelihood at the ILM boundary are calculated. Note that the ILM boundary likelihood calculation method is not limited to this. For example, the ILM boundary likelihood may be calculated using curve approximation.

In step S1003, the analysis unit 14 determines, using the ILM boundary likelihood calculated in step S1002, whether to correct the ILM boundary. In the embodiment, if an ILM boundary likelihood calculated for the vitreous-cortex candidate is equal to or higher than a predetermined value and is higher than an ILM boundary likelihood calculated for the ILM boundary at the same position (YES in step S1003), it is determined to correct the ILM boundary. If it is determined to correct the ILM boundary, the process advances to step S1004. If these conditions are not satisfied (NO in step S1003), it is determined that the vitreous-cortex candidate is the vitreous cortex, and the process advances to step S1006. Note that the determination method is not limited to this. For example, an identification unit may make a determination using the ILM boundary likelihood as a feature amount.

In step S1004, for a vitreous-cortex-candidate area determined in step S1003 to correct the ILM, the analysis unit 14 corrects the ILM boundary using position information of the vitreous-cortex candidate in this area. In the embodiment, all pieces of information such as ILM boundary information are saved in the structure-information map, so this area on the ILM boundary structure-information map is rewritten by position information of the vitreous-cortex candidate. In step S1005, the analysis unit 14 appends, to the area where the ILM boundary has been corrected in step S1004, a label representing that a cyst exists. In the embodiment, a structure-information map about the cyst is newly created, and the "cyst" label is appended to the A-scan in the ILM-corrected area.

In step S1006, for a vitreous-cortex-candidate area determined in step S1003 to be the vitreous cortex, the analysis unit 14 appends the "vitreous cortex" label to an A-scan which forms the area.

In step S1007, the analysis unit 14 checks whether an area which has not been determined exists among the areas of vitreous-cortex candidates on the structure-information map. If all areas have been determined (YES in step S1007), the process ends. If an undetermined area exists, the process returns to step S1002 to perform determination processing for an undetermined area.

Figure 13C:
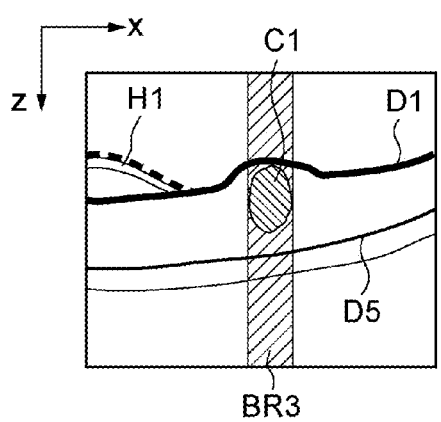
Figure 13D:
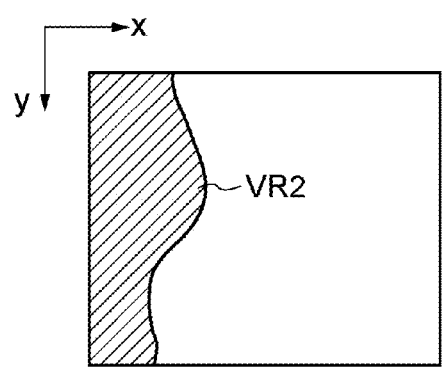
Figure 13E:
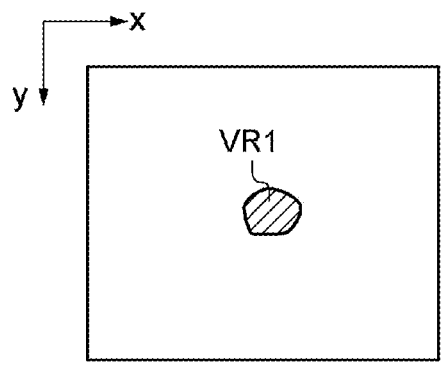

By the above-described processing, a label indicating the presence/absence of a cyst is appended to an A-scan. In a B-scan tomogram as shown in FIG. 13C, BR3 indicating a cyst area can be superimposed. When the ILM boundary is corrected, a portion between an ILM boundary after the correction and an ILM boundary before the correction may be regarded as a cyst portion and the cyst C1 may be displayed identifiably, as shown in FIG. 13C. In a C-scan tomogram, the area VR2 where the vitreous cortex floats may be superimposed as in FIG. 13D, or the cyst area VR1 may be superimposed and displayed as in FIG. 13E.

As described above, according to the second embodiment, an error can be corrected in consideration of the continuity of the retina layer structure by analyzing a retina layer structure on the map. Further, structure information can be specified in more detail, including the presence/absence of the vitreous cortex or a cyst.

According to the present invention, a cause of changing a layer structure, which is necessary for high-precision image analysis, can be specified from the tomogram of the retina.

Although the above embodiments have described an example of implementing the present invention mainly by software, an application of the present invention is not limited to this. For example, it will readily occur to those skilled in the art that the present invention is implemented by hardware by mounting the above-mentioned functional blocks as circuits. Only some of functional blocks executed by the intervention of a program in the embodiments may be mounted as a dedicated image processing board.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-264294, filed Nov. 26, 2010, which is hereby incorporated by reference herein in its entirety.

What is claimed is:

1. An image processing apparatus which processes a plurality of tomographic images obtained by acquiring, along a direction crossing a section along a thickness direction of a retina, a plurality of tomographic images each including the section, comprising:
a detection unit configured to detect a predetermined layer in the retina from the plurality of tomographic images;
an appending unit configured to append structure information to a region which is a portion of the predetermined layer; and
a generation unit configured to generate a two-dimensional image in which the region to which the structure information has been appended is mapped onto a plane crossing the thickness direction.

2. The apparatus according to claim 1, wherein said appending unit appends, as the structure information to the region, an artifact attribute representing that an artifact exists, and
wherein said appending unit appends, to another region of the predetermined layer, an artifact attribute representing that no artifact exists.

3. The apparatus according to claim 2, further comprising a determining unit configured to determine a type of the artifact based on one of a size and shape of an artifact area where the artifact attribute representing that an artifact exists is mapped in the two-dimensional image generated by said generation unit.

4. The apparatus according to claim 3, wherein said detection unit detects an inner limiting membrane (ILM) boundary and an inner and outer segments (IS/OS) boundary of the retina for each line along the thickness direction on the tomographic images, and
wherein when said detection unit has not detected the IS/OS boundary, said appending unit appends, to the line, the artifact attribute representing that an artifact exists.

5. The apparatus according to claim 3, wherein when an area of the artifact area in the two-dimensional image is not smaller than a predetermined value and a ratio of the artifact area to a rectangle area circumscribing the artifact area is not smaller than a predetermined value, said determining unit determines that the artifact is caused by a hemorrhage, and in another case, determines that the artifact is caused by a blood vessel.

6. The apparatus according to claim 3, further comprising:
an acquisition unit configured to acquire, for each line along the thickness direction of the tomographic images, structure information indicating the boundary position of the predetermined layer detected by said detection unit; and
a display unit configured to display one of the tomographic images, and display the boundary position indicated by the structure information for each line identifiably in the one of the tomographic images,
wherein said display unit displays a line having the artifact attribute representing that an artifact exists, to be able to identify the type determined by said determining unit in a display of the one of the tomographic images.

7. The apparatus according to claim 1, further comprising a unit configured to detect a discontinuity of an inner limiting membrane (ILM) boundary in the two-dimensional image, at a boundary of an area formed by a line along the thickness direction of the tomographic images, on which said detection unit detects both a vitreous cortex and the ILM boundary, thereby determining whether a cyst exists in the area.

8. The apparatus according to claim 1, further comprising:
a determining unit configured to determine continuity of a first boundary in the thickness direction at a boundary portion of a continuous area of the two-dimensional image in which there is a line along the thickness direction of the tomographic images, on which said detection unit detects separation of the first boundary and a second boundary; and
a correcting unit configured to decide, based on the continuity determined by said determining unit, whether the separation exists, and correcting a detection result of said detection unit based on the decision.

9. The apparatus according to claim 8, wherein a boundary of a first layer is a vitreous cortex, and a boundary of a second layer is an inner limiting membrane (ILM) boundary of a retina, and
wherein said correcting unit corrects the vitreous cortex to the ILM boundary, and appends information representing the presence of a cyst to structure information of the line.

10. An image processing method in an image processing apparatus which processes a plurality of tomographic images obtained by acquiring, along a direction crossing a section along a thickness direction of a retina, a plurality of tomographic images each including the section, the method comprising:
a detection step of detecting a predetermined layer in the retina from the plurality of tomographic images;
an appending step of appending structure information to a region which is a portion of the predetermined layer detected in the detection step; and
a generation step of generating a two-dimensional image in which the region to which the structure information has been appended is mapped onto a plane crossing the thickness direction.

11. A non-transitory computer-readable medium storing a program for causing a computer to execute each step of an image processing method defined in claim 10.

12. An image processing apparatus for processing a three-dimensional image comprising a plurality of tomographic images of a retina, the apparatus comprising:
a detection unit configured to detect a predetermined layer of the retina in the plurality of tomographic images; and
a determination unit configured to determine a type of a region in a two-dimensional image in which the predetermined layer detected by said detection unit is mapped onto a plane crossing a thickness direction of the retina, based on a state of the region, wherein the region is a portion of the predetermined layer and has not been detected in the predetermined layer by said detection unit.

13. An image processing method for processing a three-dimensional image comprising a plurality of tomographic images of a retina, the method comprising:
detecting a predetermined layer of the retina in the plurality of tomographic images; and
determining a type of a region in a two-dimensional image in which the predetermined layer detected in said detecting step is mapped onto a plane crossing a thickness direction of the retina, based on a state of the region, wherein the region is a portion of the predetermined layer and has not been detected in the predetermined layer in said detection step.

14. A non-transitory computer-readable medium storing a program for causing a computer to execute an image processing method defined in claim 13.

15. An image processing apparatus for processing a three-dimensional image comprising a plurality of tomographic images of a retina, the apparatus comprising:
a detection unit configured to detect a predetermined layer of the retina in the plurality of tomographic images; and
a generating unit configured to generate a two-dimensional image in which a region, which is a portion of the predetermined layer and has not been detected in the predetermined layer by said detection unit, is mapped onto a plane crossing a thickness direction of the retina.

16. An image processing method for processing a three-dimensional image comprising a plurality of tomographic images of a retina, the method comprising:
detecting a predetermined layer of the retina in the plurality of tomographic images; and
generating a two-dimensional image in which a region, which is a portion of the predetermined layer and has not been detected in the predetermined layer in the step of detecting, is mapped onto a plane crossing a thickness direction of the retina.

17. A non-transitory computer-readable medium storing a program for causing a computer to execute an image processing method defined in claim 16.

18. An image processing apparatus for processing a three-dimensional image comprising a plurality of tomographic images of a retina, the apparatus comprising:
a detection unit configured to detect a predetermined layer of the retina in the plurality of tomographic images; and
a determination unit configured to determine a type of an artificial region which is a portion of the predetermined layer based on a state of a region in a two-dimensional image in which the artificial region is mapped onto a plane crossing a thickness direction of the retina.

19. An image processing method for processing a three-dimensional image comprising a plurality of tomographic images of a retina, the method comprising:
detecting a predetermined layer of the retina in the plurality of tomographic images; and
determining a type of an artificial region which is a portion of the predetermined layer based on a state of a region in a two-dimensional image in which the artificial region is mapped onto a plane crossing a thickness direction of the retina.

20. A non-transitory computer-readable medium storing a program for causing a computer to execute an image processing method defined in claim 19.

21. An image processing apparatus for processing a three-dimensional image comprising a plurality of tomograms of a retina, the apparatus comprising:
a detection unit configured to detect a predetermined layer of the retina in the plurality of tomographic images; and
a generating unit configured to generate a two-dimensional image in which an artificial region, which is a portion of the predetermined layer, is mapped onto a plane crossing a thickness direction of the retina.

22. An image processing method for processing a three-dimensional image comprising a plurality of tomographic images of a retina, the method comprising:

detecting a predetermined layer of the retina in the plurality of tomographic images; and generating a two-dimensional image in which an artificial region, which is a portion of the predetermined layer, is mapped onto a plane crossing a thickness direction of the retina.

23. A non-transitory computer-readable medium storing a program for causing a computer to execute an image processing method defined in claim 22.

24. An image processing apparatus operable to process a plurality of tomographic images each extending in a thickness direction of a retina, the image processing apparatus comprising:

a detection unit configured to detect a predetermined layer in the retina from the plurality of tomo graphic images;

an appending unit configured to append structure information to a region which is a portion of the predetermined layer; and a generation unit configured to generate a two-dimensional image comprising a plane crossing the thickness direction of the retina, the plane having mapped thereon the region to which the structure information has been appended.

25. An image processing method of processing a plurality of tomographic images each extending in a thickness direction of a retina, the image processing apparatus comprising:

detecting a predetermined layer in the retina from the plurality of tomographic images;

appending structure information to a region which is a portion of the predetermined layer; and generating a two-dimensional image comprising a plane crossing the thickness direction of the retina, the plane having mapped thereon the region to which the structure information has been appended.

26. A non-transitory computer-readable medium storing a program for causing a computer to execute an image processing method defined in claim 25.

* * * * *